(12) United States Patent
Clark

(10) Patent No.: US 12,114,977 B2
(45) Date of Patent: Oct. 15, 2024

(54) SYSTEM AND METHOD FOR THE REAL-TIME, NONINVASIVE AND CONTINUOUS IN VIVO SENSING OF STRESS

(71) Applicant: Anthony L. Clark, Saratoga, CA (US)

(72) Inventor: Anthony L. Clark, Saratoga, CA (US)

( * ) Notice: Subject to any disclaimer, the term of this patent is extended or adjusted under 35 U.S.C. 154(b) by 201 days.

(21) Appl. No.: 17/372,450

(22) Filed: Jul. 10, 2021

(65) Prior Publication Data

US 2023/0020820 A1  Jan. 19, 2023

(51) Int. Cl.
*A61B 5/16* (2006.01)
*A61B 5/00* (2006.01)
*A61B 5/01* (2006.01)

(52) U.S. Cl.
CPC ............ *A61B 5/165* (2013.01); *A61B 5/0002* (2013.01); *A61B 5/01* (2013.01); *A61B 5/6826* (2013.01); *A61B 5/7405* (2013.01); *A61B 5/742* (2013.01); *A61B 2562/0271* (2013.01)

(58) Field of Classification Search
CPC ......... A61B 5/165; A61B 5/0002; A61B 5/01; A61B 5/6826; A61B 5/7405; A61B 5/742; A61B 2562/0271
See application file for complete search history.

(56) References Cited

U.S. PATENT DOCUMENTS

| | | | | |
|---|---|---|---|---|
| 3,585,381 A | * | 6/1971 | Hodson | G02F 1/132 349/21 |
| 3,720,623 A | * | 3/1973 | Cartmell | G02F 1/132 428/402.2 |
| 3,802,945 A | * | 4/1974 | James | B44F 1/14 428/1.5 |
| 3,951,133 A | * | 4/1976 | Reese | A61B 5/015 600/549 |
| 4,220,016 A | * | 9/1980 | Frenger | A44C 15/0005 63/14.9 |
| 4,450,843 A | * | 5/1984 | Barney | A61B 5/02438 600/549 |
| 4,747,413 A | * | 5/1988 | Bloch | G01K 13/20 600/549 |
| 4,819,656 A | * | 4/1989 | Spector | A61B 5/486 128/905 |
| 5,647,834 A | * | 7/1997 | Ron | A61B 5/16 704/E15.041 |
| 5,813,766 A | * | 9/1998 | Chen | A61B 5/6838 374/141 |

(Continued)

FOREIGN PATENT DOCUMENTS

CN  201200410 Y  *  3/2009
CN  103957777 A  *  7/2014  ............. A61B 5/002

(Continued)

OTHER PUBLICATIONS

Mahmud, Md Shaad et al., SensoRing: An Integrated Wearable System for Continuous Measurement of Physiological Biomarkers, IEEE (Year: 2018).*

(Continued)

*Primary Examiner* — Sean P Dougherty

(57) ABSTRACT

The present disclosure pertains to a wearable electronic device for the novel sensing of physiologically presented symptoms of stress corresponding to changes in a finger skin temperature biomarker.

2 Claims, 6 Drawing Sheets

(56) References Cited

U.S. PATENT DOCUMENTS

| | | | | |
|---|---|---|---|---|
| 5,964,701 | A * | 10/1999 | Asada | A61B 5/6826 600/300 |
| 6,102,846 | A * | 8/2000 | Patton | G16H 30/40 600/26 |
| 6,402,690 | B1 * | 6/2002 | Rhee | A61B 5/0002 600/323 |
| 6,675,744 | B1 * | 1/2004 | Levan | A01K 27/006 119/858 |
| 8,797,331 | B2 * | 8/2014 | Sano | A61B 5/369 345/475 |
| 9,064,390 | B1 * | 6/2015 | Clark | G08B 5/36 |
| 9,711,060 | B1 * | 7/2017 | Lusted | A61B 5/02416 |
| 10,732,722 | B1 * | 8/2020 | Heraz | G06V 40/10 |
| 2003/0009087 | A1 * | 1/2003 | Keirsbilck | A61B 5/6806 600/300 |
| 2007/0118045 | A1 * | 5/2007 | Naghavi | A61B 5/01 600/549 |
| 2007/0225614 | A1 * | 9/2007 | Naghavi | A61B 5/01 600/549 |
| 2007/0266479 | A1 * | 11/2007 | Lanzo | A61B 5/165 2/400 |
| 2008/0021344 | A1 * | 1/2008 | Jung | A61B 5/01 600/549 |
| 2008/0077044 | A1 * | 3/2008 | Nakayama | A61B 5/01 600/549 |
| 2008/0081963 | A1 * | 4/2008 | Naghavi | A61B 5/6806 600/301 |
| 2009/0002178 | A1 * | 1/2009 | Guday | G06F 3/0346 340/573.1 |
| 2009/0009284 | A1 * | 1/2009 | Sako | G16Z 99/00 340/5.82 |
| 2009/0156887 | A1 * | 6/2009 | Hsu | A61M 21/02 600/27 |
| 2010/0016742 | A1 * | 1/2010 | James | A61B 5/02405 600/509 |
| 2010/0069724 | A1 * | 3/2010 | Leuthardt | G16H 20/70 600/301 |
| 2011/0022332 | A1 * | 1/2011 | Kailas | G16H 50/20 702/42 |
| 2011/0137137 | A1 * | 6/2011 | Shin | A61B 5/0059 600/301 |
| 2011/0201960 | A1 * | 8/2011 | Price | A61B 5/01 600/300 |
| 2011/0245633 | A1 * | 10/2011 | Goldberg | A61B 5/165 600/301 |
| 2012/0083710 | A1 * | 4/2012 | Yarden | A61B 5/6826 600/549 |
| 2013/0137996 | A1 * | 5/2013 | Sanchez Avila | A61B 5/7278 600/483 |
| 2013/0183646 | A1 * | 7/2013 | Lusted | A61B 5/6826 434/236 |
| 2014/0078694 | A1 * | 3/2014 | Wissmar | A61B 5/681 361/749 |
| 2014/0085077 | A1 * | 3/2014 | Luna | A61B 5/0205 340/539.11 |
| 2014/0218187 | A1 * | 8/2014 | Chun | G08B 21/06 340/439 |
| 2015/0182129 | A1 * | 7/2015 | Colley | A61B 5/746 600/301 |
| 2015/0182160 | A1 * | 7/2015 | Kim | A61B 5/742 600/301 |
| 2015/0186609 | A1 * | 7/2015 | Utter, II | A61B 5/742 600/301 |
| 2015/0206000 | A1 * | 7/2015 | el Kaliouby | A61B 5/165 382/118 |
| 2015/0220109 | A1 * | 8/2015 | von Badinski | G04G 21/02 368/10 |
| 2015/0293926 | A1 * | 10/2015 | Yang | H04W 4/029 707/610 |
| 2015/0358415 | A1 * | 12/2015 | Cronin | G06Q 50/01 709/217 |
| 2016/0066827 | A1 * | 3/2016 | Workman | A61B 5/742 600/340 |
| 2016/0066839 | A1 * | 3/2016 | Ikeda | A61B 5/01 600/549 |
| 2016/0246326 | A1 * | 8/2016 | von Badinski | A61B 5/14532 |
| 2016/0317060 | A1 * | 11/2016 | Connor | G16H 20/60 |
| 2017/0011210 | A1 * | 1/2017 | Cheong | H04W 4/00 |
| 2017/0215745 | A1 * | 8/2017 | Felix | A61B 5/7225 |
| 2017/0330471 | A1 * | 11/2017 | Subiakto | G11B 33/025 |
| 2017/0366213 | A1 * | 12/2017 | Camacho Perez | A61B 5/02055 |
| 2018/0014739 | A1 * | 1/2018 | Eleftheriou | G06K 9/00 |
| 2018/0042540 | A1 * | 2/2018 | Kinnunen | A61B 5/16 |
| 2018/0110460 | A1 * | 4/2018 | Danson | A61B 5/14542 |
| 2018/0120892 | A1 * | 5/2018 | von Badinski | A61B 5/7264 |
| 2018/0279940 | A1 * | 10/2018 | Campbell | A61B 5/0059 |
| 2019/0223737 | A1 * | 7/2019 | Tzvieli | G02B 27/017 |
| 2019/0298172 | A1 * | 10/2019 | Mahmud | A61B 5/165 |
| 2019/0351912 | A1 * | 11/2019 | Woo | B60H 1/00964 |
| 2019/0371344 | A1 * | 12/2019 | Noh | G06V 40/174 |
| 2020/0261008 | A1 * | 8/2020 | Lee | A61B 5/6832 |
| 2020/0281525 | A1 * | 9/2020 | Mills | A61B 5/0533 |
| 2020/0327822 | A1 * | 10/2020 | Marascu | G16H 50/20 |
| 2021/0059542 | A1 * | 3/2021 | Gopalakrishnan | G06Q 50/01 |
| 2021/0290131 | A1 * | 9/2021 | Kumar | A61B 5/0022 |
| 2021/0407684 | A1 * | 12/2021 | Pho | G06F 16/285 |
| 2022/0061674 | A1 * | 3/2022 | Park | A61B 5/6815 |
| 2022/0102015 | A1 * | 3/2022 | Aoun | G16H 20/10 |
| 2022/0233119 | A1 * | 7/2022 | Shelton, IV | A61B 5/117 |
| 2022/0287622 | A1 * | 9/2022 | Thigpen | A61B 5/0816 |

FOREIGN PATENT DOCUMENTS

| | | | | |
|---|---|---|---|---|
| CN | 207912696 U | * | 9/2018 | |
| CN | 211409030 U | * | 9/2020 | |
| JP | 08126614 A | * | 5/1996 | |
| JP | 2022040945 A | * | 3/2022 | |
| WO | WO-2007013105 A1 | * | 2/2007 | A61B 5/01 |
| WO | WO-2020065081 A1 | * | 4/2020 | A61B 5/024 |

OTHER PUBLICATIONS

Mahmud, Md Shaad et al., An Integrated Wearable Sensor for Unobtrusive Continuous Measurement of Autonomic Nervous System, IEEE Internet of Things Journal, vol. 6, No. 1, pp. 1104-1113 (Year: 2019).*

Stress Market, Stress Thermometer (TM), Nov. 27, 2020, https://www.andrews.edu/services/ctcenter/prevention/stress_thermometer_instructions.pdf (Year: 2020).*

N. Ali et al., "Salivary Alpha-Amylase as a Biomarker of Stress in Behavioral Medicine," International Journal of Behavioral Medicine, vol. 27, pp. 337-342, 2020.

Caltech, "Sweat Sensor Detects Stress Levels; May Find Use in Space Exploration," Feb. 26, 2020. [Online]. Available: https://www.caltech.edu/about/news/sweat-sensor-detects-stress-levels-may-find-use-space-exploration. [Accessed Mar. 18, 2021].

S. Laborde, et al., "Heart Rate Variability and Cardiac Vagal Tone in Psychophysiological Research—Recommendations for Experiment Planning, Data Analysis, and Data Reporting," Front. Physchol., vol. 8, No. 213, pp. 1-18, 2017.

G. Shivakumar et al., "Galvanic Skin Response: A Physiological Sensor System for Affective Computing," International Journal of Machine Learning and Computing, vol. 3, No. 1, pp. 31-34, 2013.

A. Arsten, "Stress weakens prefrontal networks: molecular insults to higher cognition," Nat Neurosci., vol. 18, No. 10. pp. 1376-1385, 2015.

S. G. Hofmann, "The Effect of Mindfulness-Based Therapy on Anxiety and Depression: A Meta-Analytic Review." 2010. [Online]. https://www.ncbi.nlm.nih.gov/pmc/articles/PMC2848393/. [Accessed Aug. 18, 2020].

CDC, "Pandemics can be stressful (managing-stress-anxiety)," 2020. [Online]. Available: https://www.cdc.gov/coronavirus/2019-ncov/daily-life-coping/managing-stress-anxiety.html. [Accessed Nov. 18, 2020].

(56) References Cited

OTHER PUBLICATIONS

P. L. Watkins, et al., "Handbook of Self-Help Therapies," 77-109, New York, 2008.
J. Corliss, "Mindfulness meditation may ease anxiety, mental stress," Jan. 8, 2018. [Online]. Available: https://www.health.harvard.edu/blog/mindfulness-meditation-may-ease-anxiety-mental-stress-201401086967. [Accessed Aug. 18, 2020].
J. W. Mason, "A Review of Psychoendocrine Research on the Pituitary-Adrenal Cortical System," Psychomatic Medicine, vol. XXX, No. 5 (Part II), pp. 576-607, 1968.
D. Goldstein, "Differential responses of components of the autonomic nervous system," in Handbook of Clinical Neurology, Elsevier B.V., 2013, pp. 13-22.
R. M. Bujis, "The autonomic nervous system: a balancing act," in Autonomic Nervous System: Handbook of Clinical Neurology, Elsevier, 2013, pp. 1-11.
D. P. Stephens, et al., "Nonnoradrenergic mechanism of reflex cutaneous vasoconstriction in men," Am J Physiol Heart Circ Physiol, pp. H1496-H1504, 2001.
M. Harker, "Psychological sweating: a systematic review focused on aetiology and cutaneous response," Skin Pharmacol Physiol., vol. 26, No. 2, pp. 92-100, 2013.
R. D. Fealey, "Interoception and the autonomic nervous system reflexes thermoregulation," in Hanbook of Clinical Neurology, Elsevier B.V., 2013, pp. 79-88.
R. Clay, "Stressed in America," 2011. [Online]. https://www.apa.org/monitor/2011/01/stressed-america. [Accessed Aug. 12, 2020].
D. Liu, "Anxiety Disorders: Diagnosis & Treatment." [Online]. https://www.ihs.gov/california/tasks/sites/default/assets/File/GPRA/C5_%20Anxiety%20Disorders%20(Liu)_508.pdf. [Accessed Aug. 15, 2020].
G. Madhav, et al., "Meditation Programs for Psychological Stress and Well-being A Systematic Review and Meta-analysis," 2014. [JAMA Online]. https://jamanetwork.com/journals/jamainternalmedicine/fullarticle/1809754. [Accessed Aug. 19, 2020].
M. Melchior, "Workplace stress precipitates depression and anxiety in young, working women and men," [Online]. https://www.ncbi.nlm.nih.gov/pmc/articles/PMC2062493/. [Accessed Aug. 18, 2020].
W. G. Chen, et al, "The Emerging Science of Interoception: Sensing, Integrating, Interpreting, and Regulating." 2020. [Online]. https://doi.org/10.1016/j.tins.2020.10.007.
CDC, "Pandemics can be stressful (managing-stress-anxiety)," 2020. [Online]. Available: https://www.cdc.gov/coronavirus/2019-ncov/daily-life-coping/managing-stress-anxiety.html. [Accessed Nov. 18, 2021].
P. L. Watkins, et al., "Handbook of Self-Help Therapies," 41-57, New York, 2007.
J. Corliss, "Mindfulness meditation may ease anxiety, mental stress," Jan. 8, 2014. [Online]. Available: https://www.health.harvard.edu/blog/mindfulness-meditation-may-ease-anxiety-mental-stress-201401086967. [Accessed Nov. 19, 2021].
D. Goldstein, "Differential responses of components of the autonomic nervous system," in Handbook of Clinical Neurology, Elsevier B.V., 2013, Abstract.
R. M. Bujis, "The autonomic nervous system: a balancing act," in Autonomic Nervous System: Handbook of Clinical Neurology, Elsevier, 2013, Abstract.
M. Harker, "Psychological sweating: a systematic review focused on aetiology and cutaneous response," Skin Pharmacol Physiol., vol. 26, No. 2, Abstract, 2013.
N. Ali, "Salivary Alpha-Amylase as a Biomarker of Stress in Behavioral Medicine," International Journal of Behavioral Medicine, vol. 27, pp. 337-342, 2020.

\* cited by examiner

SYSTEM AND METHOD FOR THE REAL-TIME, NONINVASIVE AND CONTINUOUS IN VIVO SENSING OF STRESS

CROSS-REFERENCE TO RELATED PATENTS AND APPLICATIONS

This application is related to and claims priority from U.S. Pat. No. 9,064,390, titled "System and Method for a Novelty Mood Sensing Sharing Device," awarded Jun. 23, 2015, the entire contents of which are incorporated herein by reference.

STATEMENT REGARDING FEDERALLY SPONSORED RESEARCH OR DEVELOPMENT

Not Applicable.

REFERENCE TO COMPACT DISC APPENDIX

Not Applicable.

BACKGROUND OF THE INVENTION

The current invention relates to a novel system and method for the real-time, noninvasive, in vivo detection and continuous monitoring of stress utilizing finger skin temperature as a physiological biomarker. In an exemplary embodiment, a smart ring implementation of the novel system and method comprises Mood Sensing Sharing Device (MSSD) technology, as defined in U.S. Pat. No. 9,064,390 (Jun. 23, 2015)—"the '390 Patent." It should be understood that the invention is not limited to the embodiments exemplified and described hereafter.

For a large majority of Americans chronic daily stress can erode quality of life, with children and work being the two most common contributors to chronic stress. Moreover, for those who have been, or who were forced to work at home because of the recent pandemic, the merging of work and home has led to a significant increase in daily stress levels: a point that has been highlighted by the CDC, which now recognizes amplified stress as a widespread COVID-19 secondary health effect.

Exemplified by COVID-19 amplified stress, causes of stress can be either exogenous or endogenous. A workplace assignment deadline, a school exam, activities requiring acute physical exertion and COVID-19 infection are all examples of exogenous (i.e., external) stressors. Endogenous stress may result from mental anxiety, from depression, from posttraumatic stress disorder (PTSD) and from fear of contracting COVID-19 for example. Regardless of the characterization, chronic stress can result in physical symptoms or bodily manifestations. Physical symptoms of stress include headaches, upset stomach, high blood pressure, chest pain, sexual dysfunction, sleep problems, obesity, anxiety and depression.

Stress triggers a fight or flight response in vivo. The fight or flight response is an intrinsic evolutionary survival mechanism that allows humans and other mammals to quickly react to a life-threatening event. Excluding epidemics and pandemics, truly life-threatening events are thankfully rare. However, many other contemporary events, such as housing insecurity and underemployment, can be perceived as life threatening. Moreover, even the anticipation or the memory of a threat may trigger the fight or flight response.

On its own, acute stress, which triggers a fight or flight response, is not health diminishing. However, the chronic activation of the flight or flight response can impair health by negatively altering an organism's homeostasis. The effects of chronic activation include depressed immune response, fatigue, diabetes, muscle atrophy, stomach ulcers, sexual dysfunction, hypertension, heart muscle damage, weakened blood vessels, cognitive impairment, anxiety and depression.

Several physiological systems primarily coordinate the fight or flight response: the central nervous system (CNS); the peripheral nervous system (PNS); and the endocrine system. The CNS consists of the brain and spinal cord. The PNS consists of those components of the nervous system that are outside of the brain and the spinal cord. The PNS provides a bidirectional interface from the CNS to the organs, limbs, and skin. The endocrine system is a glandular communication system, which regulates hormones. The CNS connection to the endocrine system is via the hypothalamus, which is nearby the pituitary gland. Communications between the CNS, PNS and endocrine system are via nerve (neuron) signaling and hormone signaling.

The PNS comprises the somatic nervous system and the autonomic nervous system (ANS). The latter is responsible for unconscious, automatic controls within the body, including the maintenance of homeostasis. The ANS is a two sided coin. On one side of the ANS coin is the sympathetic nervous system (SNS), which is responsible for how the body reacts to danger and stressors-the fight or flight response. The parasympathetic nervous system (PSNS) is on the other side of the ANS coin. The PSNS is generally inhibited during a stress response. However, after a threat has subsided, the PSNS acts to return the body to its pre-stress state. The SNS and PSNS usually work in an antagonistic fashion to achieve homeostasis. If the SNS is the match that lights the stress response flame, then the PSNS is the extinguisher that helps to put the flame out.

Mechanistically, the stress (fight or flight) response begins in the brain; more specifically in the amygdala, the center for emotional processing. Upon the experience of a stressful event or perceived danger, the amygdala sends an alert to the hypothalamus. After prompting by the amygdala, the hypothalamus signals the pituitary gland, which in turns actuates the adrenal medulla, the inner part of the adrenal glands, to produce epinephrine (adrenaline), norepinephrine (noradrenaline) and acetylcholine. The former two comprise adrenergic signaling. The latter is associated with muscarinic signaling.

Regarding fight or flight, the effect of adrenergic signaling depends on the ratio of alpha and beta receptors at an interoceptor (e.g., a receiving organ cell). Stress induced neurotransmitter signaling can cause among other possible actions the following to occur:

Increased heart rate and more forceful contractions;
Faster blood flow to the primitive areas of the brain and skeletal muscles;
Relaxed airway muscles;
Narrowed blood vessels (vasoconstriction), to increase blood pressure and reduce blood flow to systems which are not critical to fight or flight;
Increased sweating for thermal regulation;
Slowed digestion;
Inhibited immune system function;
Dilated pupils; and
Halted production of sex hormones.

Additionally, the hypothalamus-pituitary-adrenal axis controls the release of glucocorticoids, including cortisol.

During stress, the anterior pituitary lobe releases adrenocorticotropic hormone (ATCH) to stimulate cortisol production in the adrenal glands. Glucocorticoids increase plasma glucose levels, which are critical for the primitive's brain functioning, via the following: promoting gluconeogenesis in the liver; inhibiting glucose uptake into the skeletal muscle and white adipose tissue (WAT); increasing protein degradation in the skeletal muscles to provide precursors for gluconeogenesis, by increasing lipolysis in WAT, to provide glycerol as a precursor for gluconeogenesis; and inhibiting the secretion of insulin in the pancreas.

The function of the body's largest organ, the skin, during a fight or flight response is of particular note for the current invention. Because there is a higher ratio of alpha receptors to beta receptors in the skin, adrenergic signaling received at blood vessels in the skin cause the blood vessels to constrict. This effectively reduces blood flow to the skin in general, including to the skin of the fingers, and contributes to the expression of the finger skin temperature biomarker. Reduced blood flow to the skin ensures more blood is available for higher priority fight or flight organs, such as the skeletal muscles. Moreover, reduced blood flow promotes clotting to minimize blood loss should a laceration occur.

Also important to the biomarker for the current invention is the activity of the sweat glands in the skin during a fight or flight response. Both increased skeletal muscle activity and increased lipolysis of WAT for gluconeogenesis contribute to an increase in core temperature during a fight or flight response. Sweating is triggered to facilitate evaporative cooling, as part of thermal regulation. Specifically, muscarinic signaling increases sweat output. The postganglionic neuron for sweat gland innervations is acetylcholine—which acts on muscarinic receptors. Once triggered, muscarinic receptors in the sweat glands within the fingers of hands increase sweat production to aid in thermal regulation.

Normally vasodilation of blood vessels would accompany sweating. However, during acute stress, vasodilation is delayed. The delay is because the fight or flight response prioritizes blood flow to the skeletal muscles and away from less essential organs such as the skin. Consequently, both sweating and vasoconstriction in the skin of the fingers concurrently occur at the onset of the fight or flight response. Increased sweating in the hands and fingers counteracts the diminished capacity of the hands to evacuate heat because of increased vasoconstriction in the blood vessels in the skin of the hands. The result is a discernible drop in finger skin temperature during a stress (fight or flight) response. Smart ring technology per the current invention can be used for the real time, noninvasive, in vivo and continuous monitoring of the finger skin temperature biomarker for the purpose of detecting levels of stress.

ANS correlated biomarkers used for the detection of stress can be divided into two categories: (1) biomarkers that comprise specific proteins and levels of those proteins within blood, urine, sweat or saliva and (2) biomarkers which are defined by changes in a readily observable physiological aspect of a subject. Regarding the first category, biomarkers used in prior art systems and methods for detecting levels of stress via ANS activity include cortisol and alpha-amylase. Regarding the second category of ANS biomarkers, prior art systems and methods for the detection of stress, include heart rate variability and galvanic skin response.

Per the taxonomy of the previous paragraph, the current invention's finger skin temperature biomarker belongs to the second category of biomarkers—which correlate levels of stress with changes to certain physiological markers within a subject. In real-time, the current invention noninvasively and continuously senses the finger skin temperature biomarker and algorithmically correlates the raw data of the biomarker into a measurement of stress.

Cortisol Biomarker. As previously discussed, the fight or flight response involves the HPA axis releasing glucocorticoids, including cortisol. During periods of stress, the pituitary gland releases ATCH to stimulate the adrenal glands to produce cortisol. Though, depending on when the cortisol level was measured, the acquired point-in-time reading may or may not correspond to a current or past fight or flight event. To circumvent the deficiency of serum and salivary cortisol levels only reflecting a single point in time, scalp hair measurements of cortisol have been proposed to offer a retrospective assessment of chronic stress. Still, a persistent obstacle to using cortisol as an effective biomarker for stress is the difficulty in measuring cortisol levels in real time, or near real time—making it extremely difficult to correlate any measured level with a specific stress inducing event. The reason for this is that collecting a saliva or serum sample and processing it within a lab minimally takes several hours from collection to result. The recent development of a wearable sweat sensor that detects cortisol levels promises quicker results.

Alpha-Amylase Biomarker. Salivary alpha amylase (sAA) has recently emerged as biomarker for ANS activity regarding stress. Alpha amylase is an enzyme that is involved in the digestion of carbohydrates and starches. As previously discussed, digestion is inhibited during a fight or flight response. As such, sAA proponents believe that a blunted sAA decline within 30 minutes of waking and higher sAA levels throughout the day are indicative of ANS dysregulation. In spite of the convenience of saliva based samples collection, real time stress assessment is still not possible with sAA. This makes it extremely difficult to correlate any measured level with a specific stress inducing event. The reason for this is that collecting a sample and processing it within a lab minimally takes several hours from collection to result. Moreover, the utility of sAA for individual assessment requires that a baseline for the individual be established. Ideally, such a baseline would comprise the collection of multiple samples per day over a period of a few weeks. Currently the costs for doing this are likely prohibitive for individual assessment and for larger group studies.

Heart Rate Variability. Heart Rate Variability (HRV) can be defined as the variation in the time interval between heart beats in a set of successive heart beats. A number of commercial HRV devices are available which utilize electrocardiography (ECG) to record and enable the assessment of a person's heartbeat. Because HRV is a measure of variance (or difference), a baseline is required—typically 24 hours of data collection is recommended. Heart rate variability reflects inputs from both the SNS and PSNS, so theoretically it should be possible to use HRV to detect stress. As previously discussed, during a stress response, the heart rate is increased and is accompanied by more forceful contractions, to more readily supply blood to those bodily systems that are prioritized during fight or flight. After the removal of the stressor, the PSNS takes over and reduces the heart rate. Thus the antagonistic setup of the SNS (acts to speed up heart rate) and PSNS (acts to slow down heart rate) drives HRV. When one or the other is predominant, HRV is lower. When SNS and PSNS are fairly balanced, then HRV is higher. Though HRV data is easy to collect, a significant challenge is the interpretation or analysis of the data. In part, the complexity of HRV data analysis is due to the fact that HRV parameters vary broadly among individuals; making it difficult to generalize findings which correlate with the biomarker. Also, there are more than 70 variables that can be calculated from HRV analysis and the parameters can be significantly affected by confounds such as user position (e.g., seated, standing and hand position), amount of movement and the type of subject (e.g., athletes and seniors). In addition to traditional electrocardiographs, smaller footprint devices in the form of fitness bands, smart watches and rings have recently been developed with integrated ECG capabilities. These devices tend to act on much shorter data collection periods, typically 3 to 5 minutes. This may limit the overall sensitivity (true positive rate) and specificity (true negative rate) of HRV devices.

Galvanic Skin Response. Galvanic skin response (GSR), also called electro dermal response (EDR), indirectly utilizes sweat to measure levels of stress. Implementations typically comprise an electrical circuit containing a couple of electrodes which have a constant voltage supplied across them. When the electrodes come in contact with the skin a conductive path is completed between the two electrodes. A current is induced between the two electrodes which is proportional to the current skin resistance level. Relatively dry skin, which is thought to physiologically be indicative of low stress, has an extremely high resistance, which may be measured as an open circuit. As previously discussed, stress triggers the fight or flight response, which (among a cascade of activities) causes increased sweat production, to contribute to evaporative cooling for thermal regulation purposes (muscarinic signaling). Sweaty skin, including sweat triggered by stress, is moister and relatively more conductive—less resistive. Thus GSR systems use changes in skin conductance as a biomarker for stress. A key issue regarding the use of GSR, for the measurement of stress, is the contribution of other confounds on the biomarker, which complicates the sensitivity of the biomarker. For individual use, this makes the establishment of a baseline an absolute necessity. A baseline should ideally comprise the collection of multiple samples per day over a period of up to a few weeks, to accommodate changes in skin hygiene protocols and other user specific confounds which may affect skin resistance. Still, the establishment of a baseline may not be sufficient to isolate the contribution of stress to any specific GSR measurement. This is because confounds, such as the type of skin moisturizer used, can be so large that they blunt the detection of any incremental stress induced skin conductance changes. This limits both the overall sensitivity and specificity of GSR devices.

A key distinguishing feature of the current invention, relative to all previous systems and methods for sensing and measuring stress, is that the current invention comprises the novel finger skin temperature biomarker. Moreover, the herein described MSSD based smart ring embodiment enables the real-time, non-invasive and continuous in vivo sensing of stress levels per the finger skin temperature biomarker. The current invention enables the earlier detection of stress, which in turn allows for the quicker application of interventions to resolve the stress. Additionally, the current invention monitors longer term patterns of stress, which can be used to better visualize chronic stress.

SUMMARY OF THE INVENTION

This invention relates to a novel system and method for the real-time, noninvasive and in vivo sensing of stress utilizing finger skin temperature as a physiological biomarker. Stress triggers the fight or flight response, which (among a cascade of activities) causes blood vessels in the skin of the fingers to constrict, resulting in reduced blood flow to the skin of the fingers (adrenergic signaling). Concurrently, stress causes increased sweat production in the fingers, to contribute to evaporative cooling for thermal regulation purposes (muscarinic signaling). A drop in finger skin temperature is the net result and is indicative of increased stress.

An exemplary embodiment of the current invention comprises an MSSD Smart Ring as defined in the '390 Patent. Per the current invention, two relevant components of MSSD technology are the following: (1) an MSSD Smart Ring, comprising a Mood Sensing Sharing Device (MSSD 11 in FIG. 1 of the '390 Patent); and (2) a Stress Monitor App, which is a Mood Sensing Sharing App (MSSA 52 in FIG. 5 of the '390 Patent). It should be understood that the invention is not limited to this embodiment, nor is it limited to other illustrative embodiments described herein.

Per the '390 Patent, an MSSD Smart Ring (MSSD in the setting of a ring 11 in FIG. 3 of the '390 Patent) comprises a mood stone (MSSD 20 in FIG. 2 of the '390 Patent), an insulator (Insulator 25 in FIG. 2 of the '390 Patent), and an electronics subsystem stone (ES 26 in FIG. 4 of the '390 Patent). Moreover per the '390 Patent, the mood stone "is of a type taught by U.S. Pat. No. 3,802,945" and the electronics subsystem "comprises at least one sensor," which in one embodiment of the '390 Patent is a temperature sensor (Sensor 45 in FIG. 4 of the '390 Patent). Thus, the mood stone, which exhibits temperature dependent iridescence, and the temperature sensor of an MSSD Smart Ring can individually or in combination be used to sense the finger skin temperature biomarker of the current invention.

Additionally, per the '390 Patent: "A smart phone, laptop computer, and tablet computer are all examples of mobile communications apparatuses, which are capable of executing a custom application." And, per the current invention, the '390 Patent described custom application is a Stress Monitor App (MSSA 52 in FIG. 5 of the '390 Patent). In an exemplary embodiment of the current invention, the mobile communications apparatus (MCA 12 in FIG. 1 and in FIG. 5 of the '390 Patent) is a smart phone, wherein the Stress Monitor App is executed.

An MSSD Smart Ring, per the current invention, when worn on a finger of either hand and when paired to a Stress Monitor App, per the current invention, enables the real-time, noninvasive, in vivo sensing, sharing and monitoring of stress levels by means of a finger skin temperature biomarker. In an exemplary embodiment of the current invention, the mood stone of an MSSD Smart Ring is used to noninvasively sense real-time state changes (e.g., transitioning from a higher temperature to a lower temperature) regarding a finger skin temperature biomarker for stress.

In an exemplary embodiment of the current invention, the sensor within the electronics subsystem of an MSSD Smart Ring is used to noninvasively sense state changes in the finger skin temperature biomarker in real time. Alternatively, the mood stone in an MSSD Smart Ring can be used to sense changes in a finger skin temperature biomarker.

In an exemplary embodiment of the current invention, an MSSD Smart Ring noninvasively and continuously senses a finger skin temperature biomarker and periodically shares raw data regarding the finger skin temperature biomarker with a paired Stress Monitor App, which algorithmically correlates the received raw data pertaining to the finger skin temperature biomarker into a measurement of stress which is presented to a wearer of the MSSD Smart Ring.

In another exemplary embodiment of the current invention, an MSSD Smart Ring noninvasively and continuously senses a finger skin temperature biomarker before algorithmically correlating the sensed finger skin temperature biomarker reading into a stress state which is then shared with a paired Stress Monitor App, which then presents the measurement of stress to a wearer of the MSSD Smart Ring.

In the case of the detection of a high level of stress, the MSSD Smart Ring forwards the measurement of the finger skin temperature biomarker to the Stress Monitor App, which then in an example embodiment suggests a conservative intervention (e.g., meditation) to a wearer of the MSSD Smart Ring via a system notification on an MCA running the Stress Monitor App. A goal of earlier stress detection is a quicker resolution of symptoms of stress.

Moreover, the Stress Monitor App of the current invention keeps longer term statistics regarding stress. Among other provided insights, the stress statistics summarize how often a user has been in a particular stress state (e.g., Medium Stress) during a specified time frame; allowing, for example, chronic stress to be more easily monitored and visualized. In an exemplary embodiment, longer term stress statistics are accessed by selecting the "History" button when it appears at the bottom right of the user interface screen within an MCA. Historical stress statistics enable the easier visualization of chronic stress.

DESCRIPTION OF THE PREFERRED EMBODIMENTS

Figure 6:
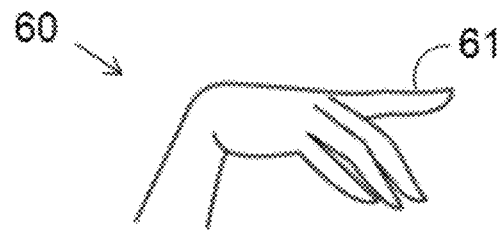
FIG. 6 illustrates a hand with the index finger extended to highlight a position to assess a finger skin temperature biomarker.

This invention relates to a novel system and method for the real-time, noninvasive and continuous in vivo sensing of stress utilizing finger skin temperature as a physiological biomarker. Stress triggers the fight or flight response, which among a cascade of activities causes blood vessels in the skin of each finger 61 (FIG. 6) to constrict, resulting in reduced blood flow to the skin of the fingers (adrenergic signaling). Concurrently, stress causes increased sweat production in the fingers, to contribute to evaporative cooling for thermal regulation purposes (muscarinic signaling). As stress increases, the combination of reduced blood flow in the fingers and increased sweating in the fingers causes a discernible drop in the finger skin temperature of each finger 61. Thus, changes in the expression of the finger skin temperature biomarker can be algorithmically correlated with changes in stress levels. In a preferred embodiment of the current invention, finger skin temperature is used as a biomarker for stress.

Figure 3:
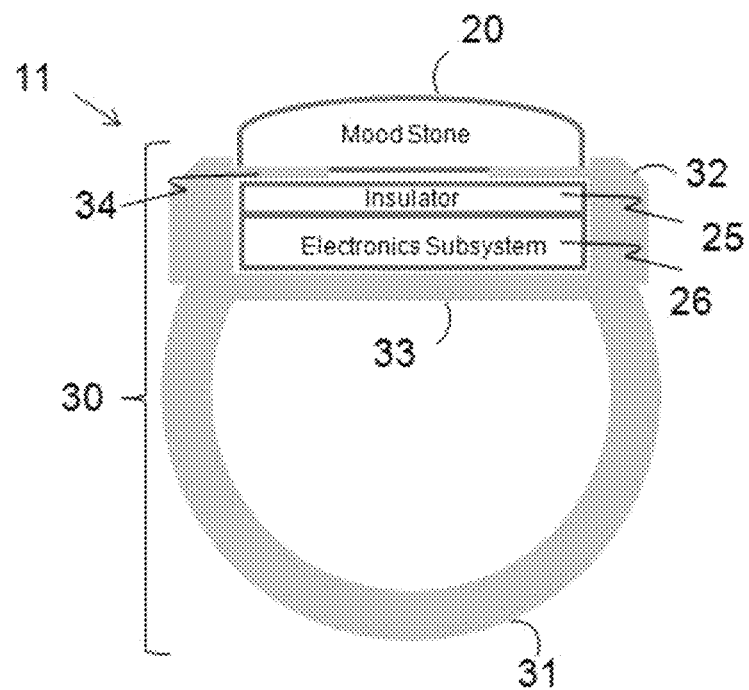
FIG. 3 is FIG. 3 of the '390 Patent and is a vertical cross section view of a mood sensing sharing device in the setting of a ring.
Figure 5:
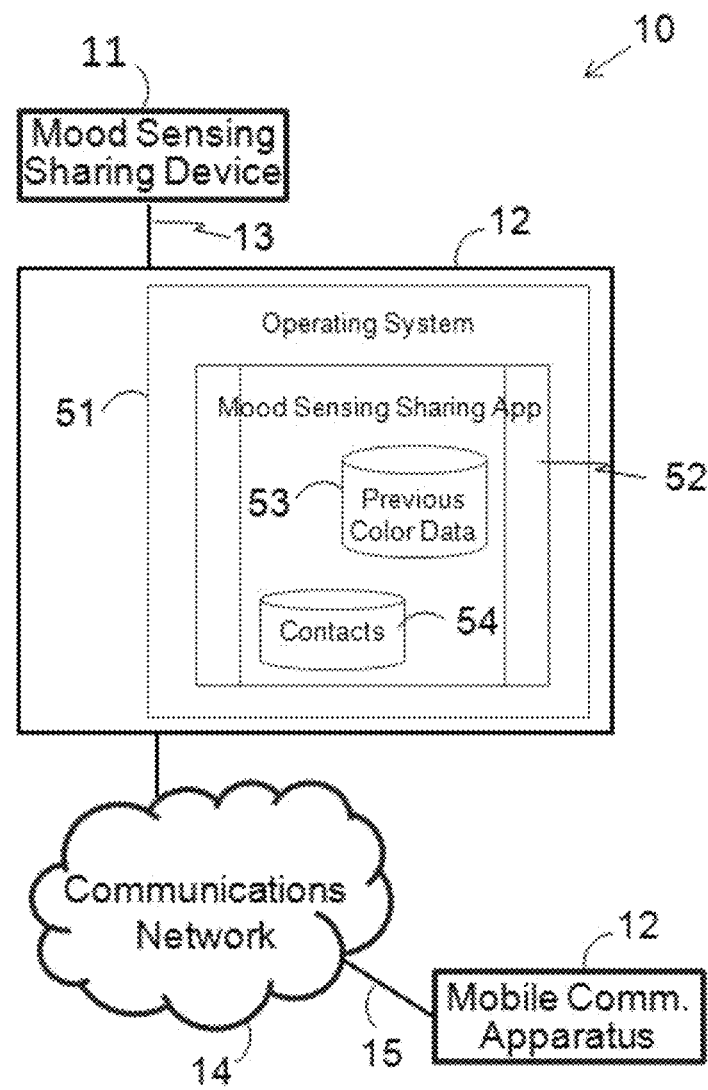
FIG. 5 is FIG. 5 of the '390 Patent and illustrates the operating environment and major data structures for a mood sensing sharing application of a mobile communications apparatus in a mood sensing sharing system.

A preferred embodiment of the current invention comprises an MSSD Smart Ring 30 as defined in the '390 Patent FIG. 3. Per the current invention, two relevant components of MSSD technology are the following: (1) an MSSD Smart Ring 30 (FIG. 3), comprising a Mood Sensing Sharing Device (MSSD) 11 (FIG. 1); and (2) a Stress Monitor App, which is a type of Mood Sensing Sharing App (MSSA) 52 (FIG. 5). An MSSD Smart Ring 30 in a preferred embodiment of the current invention continuously senses a finger skin temperature biomarker of a finger 61. It should be understood that the current invention is not limited to this embodiment, nor is the current invention limited to other illustrative embodiments described herein.

With respect to FIG. 3, an MSSD Smart Ring 30, which is worn on a finger 61 of a hand 60, comprises a mood stone 20, an insulator 25, and an electronics subsystem (ES) 26—within a ring setting 32 of a chassis 34. In a preferred embodiment of the current invention, the insulator 25 of an MSSD Smart Ring 30 is omitted such that the MSSD Smart Ring 30 comprises a mood stone 20 and an ES 26. In another exemplary embodiment of the current invention, both the insulator 25 and the mood stone 20 of an MSSD Smart Ring 30 are omitted such that the MSSD Smart Ring 30 comprises an ES 26.

In a preferred embodiment of the current invention, an MSSD Smart Ring's chassis 34 per FIG. 3 is comprised of a 3D printed carbon fiber material, which is black in color.

As taught in the '390 Patent, a mood stone 20 of an MSSD Smart Ring 30 is a Thermochromic Liquid Crystal decorative ring stone. In a preferred embodiment of the current invention, the mood stone 20 is per the TABLE 1 specification.

TABLE 1

| Mood Stone 20 of a MSSD Smart Ring 30 |
| --- |
| The gemstone shaped dome 21 comprises a clear, non-faceted glass, which is square in shape –20.0 millimeters (mm) in width, 20.0 mm in length and 5.8 mm in height at its apex. |
| The clear substrate 22 is a clear polyester plastic sheet with an adhesive layer, having a combined thickness of 180.0 microns. |
| The liquid crystal layer 23 is a microencapsulated Thermochromic Liquid Crystal ink deposited to a thickness of 50.0 microns on top of a black plastic backing 24. |
| The start temperatures for the color range of the liquid crystal layer 23 are as follows: Red Start (25.0° C.); Green Start (26.0° C.); and Blue Start (30.0° C.). A Black color is displayed below 25.0° C. |
| The black backing 24 is a black colored polyester plastic sheet and adhesive layer, which are a combined 180.0 microns in thickness. |

The mood stone 20, which exhibits factory tunable temperature dependent iridescence per its Thermochromic Liquid Crystal composition, can be used to continuously sense a finger skin temperature biomarker of a finger 61. In a preferred embodiment of the current invention, each of the mood stone 20 color states ("Blue," "Green," "Red" and "Black") is inferred to a stress level; respectively "Blue," "Green," "Red" and "Black" correspond to stress levels "None," "Low," "Medium" and "High." Thus, per the specification in TABLE 1, a mood stone 20 of an MSSD Smart Ring 30 provides a continuous indication of the stress being experienced by a wearer of an MSSD Smart Ring 30.

Figure 4:
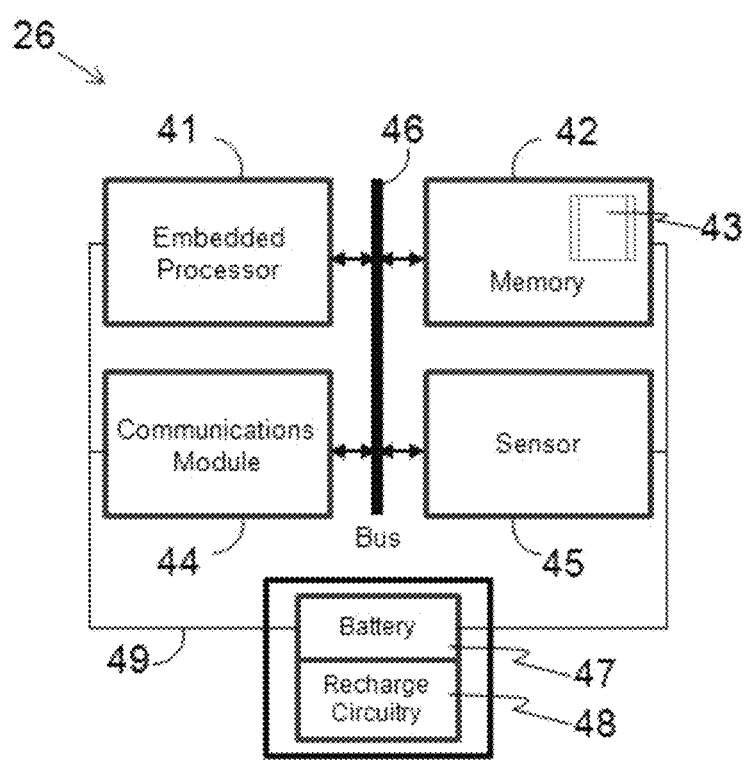
FIG. 4 is FIG. 4 of the '390 Patent and is a block diagram of an embodiment of the electronics subsystem of a mood sensing sharing device.

Small physical size, low power consumption, and low cost are desirable characteristics for any implementation of an electronics subsystem 26. Referring to FIG. 4, in a preferred embodiment of an ES 26 per the current invention, components therein the ES 21 are implemented as a mixed signal system-on-a-chip (SoC), comprising a single chip substrate, as an application specific integrated circuit (ASIC), using a 65 nm technology process. In other embodiments of an ES 21, components therein are implemented in a system-in-a-package (SiP), comprising multiple chips in a chip carrier, as an ASIC or field programmable gate array (FPGA), using a 65 nm or other size technology process.

Again referring to FIG. 4, an ES 26 consists of one or more sensors 45, a microprocessor 41, memory 42, wireless connectivity via a communications module 44 and a powering-charging element comprising a battery 47 and recharge circuitry 48. The ES 26 is housed within an MSSD Smart Ring chassis 30 per FIG. 3.

In a preferred embodiment of the current invention, an MSSD Smart Ring's microprocessor 41 is a low power, mixed signal 16-bit ARM® based micro-controller, having both integrated digital-to-analog and analog-to-digital converters.

In a preferred embodiment of the current invention, an MSSD Smart Ring's memory 42 is an NAND flash memory module having a density of 256 Megabytes and a having a bus width of 16-bits. Again referring to FIG. 4, (within an MSSD Smart Ring 30) a memory 42 contains a sensor service routine 43. The sensor service routine 43 is software, executing within a Linux based embedded operating system, for example, which enables the current state of a finger skin temperature biomarker, per the current invention, to be sensed and shared with at least one MCA 12. Referring to FIG. 4, in a preferred embodiment of the current invention, the sensor service routine 43, of the electronics subsystem 26, comprises the following functions: the establishment of a communications connection 13, through a communications module 44, using existing connection setup protocols; the interpretation of raw data from a sensor 45 to determine the color of a mood stone 20; the characterization of information from a sensor 45 to determine the current state of a finger skin temperature biomarker per the current invention; the sending of an indication of the color of a mood stone 20 over a communications connection 13; and the sending of a temperature reading of a finger skin temperature biomarker over a communications connection 13.

In a preferred embodiment of the current invention, a sensor 45 is a programmable, low operating current, digital temperature thermometer having the following characteristics: a minimum range of 20 degrees C. to 40 degrees C.; a minimum resolution of 0.5 degrees C.; a minimum accuracy of 0.5 degrees C.; and a response time of less than 1 second.

In a preferred embodiment of the current invention, temperature readings per a sensor 45 corresponding to a finger skin temperature biomarker of a finger 61 are communicated to a Stress Monitoring App 52 operating in an MCA 12 via a communications module 44 over a communications connection 13 at a rate of one temperature reading every thirty seconds.

In a preferred embodiment of the current invention, a sensor 45, in an MSSD Smart Ring 30, independently senses a finger skin temperature biomarker of a finger 61.

Figure 1:
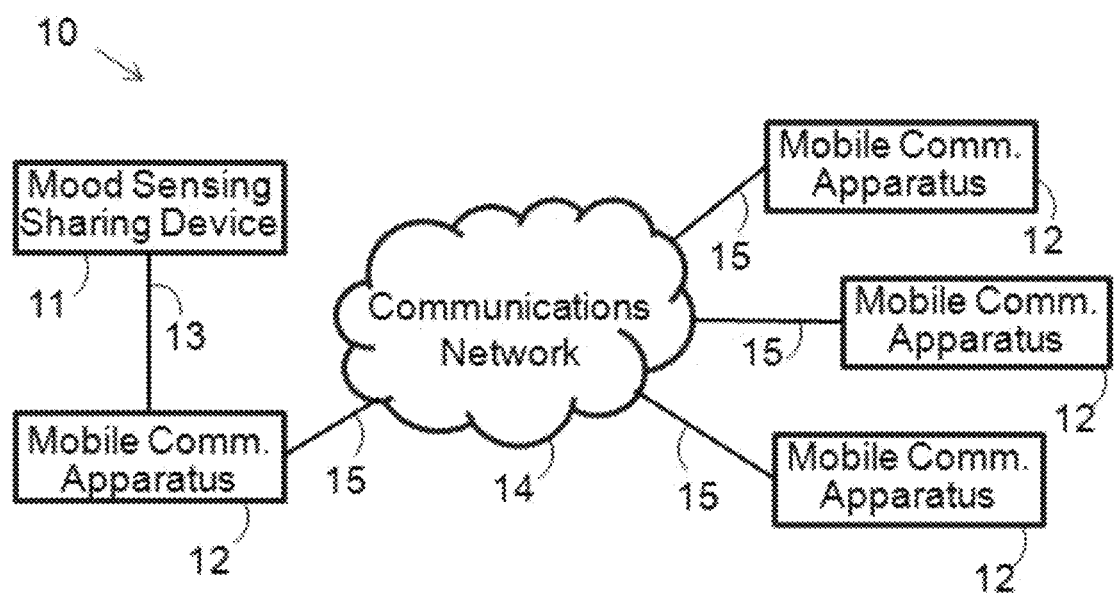
FIG. 1 is FIG. 1 of the '390 Patent and is a block level diagram of a mood sensing sharing system.
Figure 2:
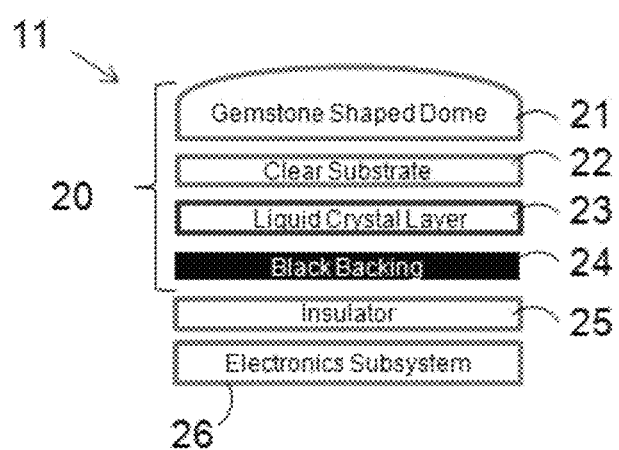
FIG. 2 is FIG. 2 of the '390 Patent and is a diagram of one implementation of a partially exploded mood sensing sharing device.

Referring to FIG. 4, wireless connectivity is provided via Communications Module 44 within an MSSD Smart Ring 30 (FIG. 3). A communications module 44 provides Bluetooth® communication, over a communications connection 13, to a paired MCA 12 (FIG. 1). In a preferred embodiment of the current invention the Bluetooth Low Energy v4.0 standard protocol is implemented over a communications connection 13.

As illustrated in the block diagram of FIG. 4, an MSSD Smart Ring's 30 powering-charging element comprises a battery 47 and recharge circuitry 48. In a preferred embodiment of the current invention, the battery 47 is a 3.7V LIPO battery, having built-in overcharge protection circuitry, and the recharge circuitry 48 comprises a USB wall charging adaptor with analog circuitry to adapt a wall outlet's AC current into a 4V DC charging current.

FIG. 5 illustrates the operating environment and major data structures for an MSSA 52 of a MCA 12 paired to an MSSD Smart Ring 30. Generally, an MCA 12 is a computing platform in the form of a smart phone, tablet computer, personal computer, or other similar device. Regarding the current invention, relevant aspects of an MCA 12 include a central processing core, memory modules, input-output modules, and a mobile operating system 51, such as Google Android or Apple iOS. An MSSA 52 is custom software, operating in an MCA 12, which enables an MCA 12 to pair with an MSSD Smart Ring 30, by means of a communications connection 13, in order to receive characterized data from a sensor 45 or a mood stone 20. Generally, an MSSA 52 of the current invention comprises the following functions: the establishment of communications connections 13 with an MSSD Smart Ring 30, the use of one or more existing connection setup protocols; the identification of an MSSD Smart Ring 30 by means of a unique identifier; and the receiving of characterized sensor 45 data or mood stone 20 data from an MSSD Smart Ring 30 over said communications connection 13.

In a preferred embodiment of the current invention, an MSSA 52 of an MCA 12, that is paired to an MSSD Smart Ring 30, is a Stress Monitor App 52, which receives and processes sensor 45 data pertaining to a finger skin temperature biomarker for a finger 61 upon which the MSSD Smart Ring 30 is worn.

In a preferred embodiment of the current invention, a Stress Monitor App 52 of an MCA 12 maps received sensor 45 data, from a paired MSSD Smart Ring 30, pertaining to a finger skin temperature biomarker for a finger 61 of a hand 60 into one of four stress states: "None" (temperature greater than or equal to 30° C.), "Low"(temperature greater than or equal to 26° C. and less than 30° C.), "Medium" (temperature greater than or equal to 25° C. and less than 26° C.) and "High" (temperature less than 25° C.).

In an exemplary embodiment of the current invention, a Stress Monitor App 52 of an MCA 12 maps received mood stone 20 color data, from a paired MSSD Smart Ring 30, pertaining to a finger skin temperature biomarker for a finger 61 of a hand 60 into one of four stress states: "None" (mood stone color blue), "Low" (mood stone color green), "Medium" (mood stone color red) and "High" (mood stone color black).

In an exemplary embodiment of the current invention, a Stress Monitor App 52 of an MCA 12 receives stress level data, from a paired MSSD Smart Ring 30 pertaining to a finger skin temperature biomarker for a finger 61 of a hand 60, that is labeled as one of the following states: "None," "Low," "Medium," and "High."

In a preferred embodiment of the current invention, when in the foreground of an operating system's 51 User Interface, a Stress Monitor App 52 of an MCA 12 echoes a paired MSSD Smart Ring's 30 mood stone's 20 color by displaying an illustrative image, which matches the received color of the mood stone 20, and which is accompanied by a message that is indicative of the wearer's current stress level: "None," "Low," "Medium," or "High" in an app view.

In a preferred embodiment of the current invention, when a Stress Monitor App 52 of an MCA 12 is in the background of the operating system's 51 User Interface and a "High" level of stress is sensed by a paired MSSD Smart Ring 30, then the Stress Monitor App 52 of the MCA 12 generates a system notification to alert a user of the occurrence of a "High" (or other) level of stress.

The Stress Monitor App of the current invention keeps longer term statistics regarding stress. Among other provided insights, the stress statistics summarize how often a user has been in a particular stress state (e.g., Medium Stress) during a specified time frame (e.g., past 3 months); allowing, for example, chronic stress to be more easily monitored and visualized. In a preferred embodiment of the current invention, each received stress indication from a paired MSSD Smart Ring 30 is kept in data storage to allow statistical analysis by a Stress Monitor App 52 of an MCA 12. In a preferred embodiment of the current invention, the longer term stress statistics (e.g., average stress level during the past 3 months) per an MSSD Smart Ring 30 can be accessed by selecting a "History" button when it appears in a view or screen of the Stress Monitor App 52 of an MCA 12.

In an exemplary embodiment of the current invention, the functionality of a Stress Monitor App 52 is implemented in the operating system of an ES 26, to form a combined smart ring and stress monitor app. The combined smart ring and stress monitor app enables the standalone real-time, noninvasive and continuous in vivo sensing of stress, utilizing finger skin temperature as a physiological biomarker, and enables the independent display of detected stress levels on the combined smart ring.

While in the foregoing, there have been described specific apparatuses and methods for the present invention, it is to be clearly understood that the provided description is exemplary and is not to limit the scope of the invention.

I claim:

1. An electronic system for sensing and displaying stress levels, comprising:
   a smart ring, the smart ring configured to sense stress levels, and a paired mobile communications apparatus, the paired mobile communications apparatus configured to display stress levels;
   the smart ring configured to be worn on a finger of a user for real- time, in vivo, non-invasive sensing of stress levels;
   the smart ring comprising an electronics subsystem, said electronics subsystem comprising a micro-controller and a sensor service routine, said micro-controller configured to execute said sensor service routine, said sensor service routine configured to continuously sense in real-time a finger skin temperature biomarker presented at a finger whereon the smart ring is worn;
   map in real-time a current finger skin temperature biomarker reading to a stress level; and
   send the mapped stress level to the paired mobile communications apparatus;
   the paired mobile communications apparatus comprising a processor, non-transitory memory, and a stress monitor app, said processor configured to execute said stress monitor app, said stress monitor app configured to;
   receive the continuously mapped stress levels from the microcontroller;
   store the continuously mapped stress levels on the non-transitory memory;
   display the continuously mapped stress levels received from the microcontroller; and
   summarize and display how often the user has been in a particular stress level during a specified time frame.

2. The electronic system for sensing and displaying stress levels in claim 1, wherein the sensor service routine is configured to send the mapped stress level to the paired mobile communications apparatus every thirty seconds.

* * * * *